United States Patent [19]

Shim

[11] 4,092,377

[45] May 30, 1978

[54] PROCESS FOR PREPARING POLYALKYLENE GLYCOL ALKYL OR HALOALKYL POLYPHOSPHONATES

[75] Inventor: Kyung S. Shim, Irvington, N.Y.

[73] Assignee: Stauffer Chemical Company, Westport, Conn.

[21] Appl. No.: 742,500

[22] Filed: Nov. 17, 1976

Related U.S. Application Data

[60] Continuation of Ser. No. 501,907, Aug. 30, 1974, abandoned, which is a division of Ser. No. 282,642, Aug. 21, 1972, Pat. No. 3,824,926.

[51] Int. Cl.² .................................................. C07F 9/40
[52] U.S. Cl. ......................................... 260/969; 260/982
[58] Field of Search ............ 260/929, 982 (U.S. only), 260/982, 969

[56] References Cited

U.S. PATENT DOCUMENTS

| 3,082,189 | 3/1963 | Mack et al. ........................ 260/982 X |
| 3,262,999 | 7/1966 | Friedman ........................... 260/929 X |
| 3,352,947 | 11/1967 | Lew .................................. 260/982 X |
| 3,578,731 | 5/1971 | Mange et al. ........................ 260/929 |
| 3,840,622 | 10/1974 | Shim ..................................... 260/929 |
| 3,986,990 | 10/1976 | Giolito ............................. 260/929 X |

*Primary Examiner*—Anton H. Sutto
*Attorney, Agent, or Firm*—William R. Robinson

[57] ABSTRACT

Polyalkylene glycol alkyl or haloalkyl polyphosphonates having the idealized formula:

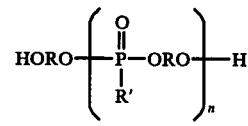

wherein R is a polyalkylene glycol residue, R' is alkyl or haloalkyl and $n$ is 1-100, are prepared by transesterifying a tertiary phosphite with a polyalkylene glycol and rearranging the resultant polyalkylene glycol alkyl or haloalkyl polyphosphite to a polyalkylene glycol alkyl or haloalkyl phosphonate by the action of heat and an Arbuzov rearrangement catalyst.

7 Claims, No Drawings

PROCESS FOR PREPARING POLYALKYLENE GLYCOL ALKYL OR HALOALKYL POLYPHOSPHONATES

This is a continuation of application Ser. No. 501,907, filed Aug. 30, 1974, now abandoned, said application being a divisional of application Ser. No. 282,642, filed Aug. 21, 1972, now U.S. Pat. No. 3,824,926.

BACKGROUND OF THE INVENTION

In the polyurethane field, increased interest is being shown in compounds which can be added to the polyurethane polymers to act as flame retardant agents. Particular interest is being shown in compounds which have functional groups reactive with the polyol or polyisocyanate used in preparing the polyurethane so that the flame retardant agent can be copolymerized into the polymer chain. One such group of reactive flame retardants are the polyalkylene glycol phosphites such as those described in U.S. Pat. No. 3,009,939. However, these materials, due to their high OH number and crosslinking tendency, are unsuitable for use in flexible urethane foams. In U.S. Pat. Nos. 3,081,331 and 3,142,651, there is disclosed a method of forming polyalkylene glycol polyphosphites having up to 10 phosphite groups in the polymer chain by reacting a trialkyl phosphite with a polypropylene glycol in a molar ratio of 2.1 to 2.5 moles of glycol per mole of phosphite. These materials are also unsuitable for use in flexible urethane foams as a result of their high OH numbers and their tendency to crosslink.

Another attempt at employing reactive flame retardants, described in U.S. Pat. Nos. 3,142,651 and 3,092,651, involves the use of polypropylene glycol poly-hydrogenphosphonates produced by a thermal polymerization. Likewise, polyalkylene glycol hydrogen polyphosphonates have also been produced by transesterifying a secondary hydrogen phosphonate with a polyalkylene glycol according to the procedure outlined in British Pat. Nos. 796,446 and 1,011,118. However, many of these materials have relatively high acidity, causing them to react with and thereby deactivate the catalyst systems generally used in the formation of polyurethane polymers such as, for example, tertiary amine compounds. The former method has the additional drawback of contamination of the product by the alkylene glycol by-product, which contaminant is not easily removed.

In order to increase the flame retardancy of some of the above described phosphorus compounds, which have low phosphorus content, the prior art has attempted to incorporate various halogen containing substituents into the above described molecules. Thus, U.S. Pat. Nos. 3,159,605 and 3,167,575, describe the reaction of halogenated methanes with these compounds. Likewise, U.S. Pat. Nos. 3,131,206 and 3,328,493, describe the reaction of chloral with them. However, these materials, like their precursors, have many drawbacks. In particular, these products have high OH numbers and low phosphorus content thereby rendering them less suitable as flame retardants in flexible urethane foams.

In addition to these above-mentioned prior art references, Review In Macromolecular Chemistry, Vol. II, N.Y.C. 1967, discloses that polyalkylene glycol alkyl phosphonates have been prepared by reacting an alkyl phosphonic acid dichloride with a polyalkylene glycol. This procedure was originally reported by Korshak et al, in Vzsokomolekuylarnye Soedineniya 2, 427–32 (1960). In a subsequent article by Tormosina et al, Khim. Khim. Tekhonol. 1968, 31–41, the polyalkylene glycol alkyl phosphonates prepared by this route are disclosed as containing unhydrolyzed chlorine and being too acidic for use in polyurethane foam. Furthermore, Korshak et al, Izv. Akad. Nauk. SSSR, Otd. Khim. Nauk. 1963(6), 1095–1100, disclose the preparation of polyalkylene glycol alkyl phosphonates by transesterifying dimethylmethylphosphonate with diethylene glycol. The product, however, is disclosed as being characterized with an acid number of from 240 to 400 mg. of KOH/gm. of sample and accordingly is also unsuitable for use in polyurethane foam.

In co-pending U.S. applications Ser. No. 166,289 filed July 26, 1971 and issued as U.S. Pat. No. 3,789,290 on Mar. 19, 1974 and Ser. No. 86,313 filed Nov. 2, 1970 and issued as U.S. Pat. No. 3,819,750 on June 25, 1974, there are disclosed novel polyalkylene glycol vinyl phosphates and novel mixed polyalkylene glycol vinyl phosphates and phosphites which are prepared by reacting a halogenated carbonyl compound with a polyalkylene glycol alkyl polyphosphite. While these vinyl phosphonates yield polyurethane foam having excellent flame retardant and physical characteristics, they have recently been found to impart a slight odor to the foam which may be considered objectionable.

SUMMARY OF THE INVENTION

Accordingly, it is one object of the present invention to provide novel polyalkylene glycol alkyl or haloalkyl polyphosphonates which are suitable as flame-retardants.

Another object of this invention is to provide polyalkylene glycol alkyl or haloalkyl polyphosphonates suitable as flame retardants for urethane foams, and in particular flexible and rigid urethane foams.

A further object of the present invention is to provide polyalkylene glycol alkyl or haloalkyl polyphosphonates which, while imparting excellent flame-retardancy to urethane foam, are further characterized by superior chemical and physical properties, such as, for example, stability and low acidity, so as to yield foams having good color, good appearance, no odor and generally good physical properties.

A further object of this invention is to provide urethane foams having incorporated therein these novel polyalkylene glycol alkyl or haloalkyl polyphosphonates.

A still further object of the present invention is to provide novel processes for the preparation of these polyalkylene glycol alkyl or haloalkyl polyphosphonates.

Further advantages of the present invention will become obvious from a reading of the disclosure which follows hereinafter.

DESCRIPTION OF THE PREFERRED EMBODIMENTS

It has now been discovered that by heating certain polyalkylene glycol alkyl polyphosphites in the presence of an alkyl halide, there is obtained polyalkylene glycol alkyl polyphosphonates which are polymers being particularly characterized by their excellent flame retardant properties and low acidity. In addition, the present polyalkylene glycol alkyl polyphosphonates are characterized by low OH numbers, lack of tendency to gel initially or crosslink in the final foamed product, high stability during and subsequent to the foam forming process, and the overall general ability to yield urethane foams which have superior flame retardancy and excellent physical properties, such as the substantial lack of scorch, discoloration, odor and other undesirable properties.

The polyalkylene glycol alkyl polyphosphonates of the present invention can be represented by an idealized formula as follows:

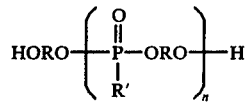 (I)

wherein R is a polyalkylene glycol residue; R' is alkyl or haloalkyl and $n$ is a number in the range of from about 1 to 100, and preferably from about 5 to 20. Preferably, R' is $C_1$–$C_{10}$ alkyl or $C_1$–$C_{10}$ haloalkyl. Haloalkyl is intended to include for example, chloromethyl, bromomethyl, chloroethyl, bromoethyl, dichloropropyl, and the like. Most preferably, however, R' is methyl. The term polyalkylene glycol residue, designated by R, is meant to define that portion remaining after two hydroxyl groups have been removed from a polyalkylene glycol having the formula:

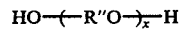

wherein R'' is an alkylene group of 2 to about 20 carbon atoms, which is straight chained, branch chained, or a mixture thereof, with the proviso that at least two carbon atoms separate successive oxygen atoms, and $x$ designates the number of repeating alkylene ether units and is normally 2 to about 20. For the purposes of the present invention, R is Formula I above, is most preferably a diethylene glycol residue.

As indicated above, Formula I represents an idealized structure of the final products of the present invention. It is clear to one skilled in the art that as a result of the polymeric nature of these polyalkylene glycol alkyl polyphosphonates of the present invention and their method of preparation, these products are complex mixtures. Thus, for example, these mixtures will include in addition to the hydroxy terminated polymers, as represented by the idealized structure of Formula I above, a statistical quantity of polymeric product wherein the terminal hydroxy groups are either partially or fully replaced by

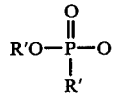

groups wherein R' is as defined above. Furthermore, the polymer products of the present invention will also include a statistical quantity of polymeric product wherein R' of Formula I above, is replaced by an R group, also as defined above, and in turn the alkyl or haloalkyl phosphonate condensates thereof. Therefore, it is to be understood that the present invention as particularly encompassed by the structure of Formula I above, is obviously intended to include these polymeric materials individually as well as in combination.

The compounds of the present invention are prepared by heating a polyalkylene glycol alkyl or haloalkyl polyphosphite which has an idealized formula as follows:

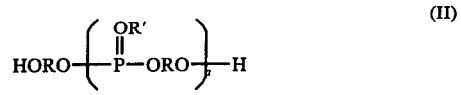 (II)

wherein R, R' and $n$ are as described above, in the presence of an alkyl or aralkyl halide. This polyphosphite of Formula II above, is formed by transesterifying a tertiary phosphite with a polyalkylene glycol in a molar ratio of from about 0.8 to about 1.5 and preferably from about 0.8 to about 1.2 moles of phosphite per mole of glycol.

The preparation of these polyalkylene glycol polyphosphites of Formula II is disclosed in the above-noted co-pending applications and in addition are disclosed and claimed in co-pending U.S. application Ser. No. 166,295 filed on July 26, 1971, by Silvio L. Giolito and abandoned in favor of continuation-in-part application Ser. No. 322,595, filed Jan. 10, 1973 which was abandoned in favor of continuation application Ser. No. 483,606 filed June 27, 1974.

The tertiary phosphite used to prepare these polyalkylene glycol alkyl or haloalkyl polyphosphite starting materials of Formula II has the general formula:

wherein each R' is as defined above. Thus, illustrative of the tertiary phosphites which can be employed are the following: trimethyl phosphite, triethyl phosphite, tripropyl phosphite, tributyl phosphite, trioctyl phosphite, dimethyl ethyl phosphite, diethyl methyl phosphite, tris(chloroethyl) phosphite, tris(2-chloropropyl) phosphite, tris(dichloropropyl) phosphite, and the like. Trimethyl and triethyl phosphite are particularly preferred, with trimethyl phosphite being most preferred.

The above described tertiary phosphite is transesterified with a polyalkylene glycol having the formula:

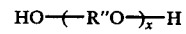

wherein R'' and $x$ are as described above. Illustrative of the polyalkylene glycols which can be employed in the present invention are the following: diethylene glycol, triethylene glycol, dipropylene glycol, tripropylene glycol, tributylene glycol, polyethylene glycols, polypropylene glycols wherein the average number of ether units is 14, trihexylene glycol and the like. Particularly preferred glycols are diethylene glycol, dipropylene glycol and tripropylene glycol, with diethylene glycol being most preferred. It is understood that the propylene glycols can be primary, secondary, or mixtures thereof.

In order to form the polyphosphite starting material of Formula II above, the tertiary phosphite and the polyalkylene glycol must be reacted in critical proportions. Thus, the tertiary phosphite should be present in an amount from about 0.8 to about 1.5 moles per mole of the glycol. The preferred range for this preparation is from about 1 to about 1.2 moles of phosphite per mole of glycol. If the glycol is reacted in quantitites substantially greater than about 1 to 1 with the phosphite, the product will contain primarily the undesirable mono, di, tri and tetraphosphites and, more importantly, will have a substantial amount of free hydroxyalkyleneoxyalkylene groups attached to the phosphite group.

Where trimethyl phosphite and diethylene glycol are utilized to prepare the polyphosphite of Formula II, it now has been found for the purposes of this invention, that it is most preferred to employ 1.1 moles of phosphite to 1 mole of glycol.

The above disclosed transesterification reaction is normally conducted by mixing the phosphite and glycol in the presence of any of the well known transesterification catalysts. Particularly useful catalysts are the alkali metal alcoholates and phenolates such as sodium methylate, sodium decylate, sodium phenolate, and the like. These catalysts are normally employed in an amount from about 0.1 to about 10 percent, by weight, of the entire reaction mixture. Again, with particular regard to the transesterification reaction between trimethyl phosphite and diethylene glycol it now has been found that no catalyst is necessary, although, obviously if desired, one may be employed. The reaction temperature should initially be kept below the boiling point of the lowest boiling reactant in order to avoid the loss of that reactant. Although the reaction can be conducted at room temperature, i.e., 20° C., it is preferred to conduct it as close to the upper limit as possible in order to increase the rate of reaction. Thus, in the case where trimethyl phosphite is employed as the tertiary phosphite, the reaction temperature is preferably within the range of 60° to 110° C. and should not be allowed to rise above 110° C. until at least one R' group on each of the phosphite molecules has been replaced with a polyalkylene glycol. This can normally be determined by monitoring the amount of methanol which has been evolved.

While the reaction can be run to completion at these temperature ranges, it has been found to be advantageous at times to raise the temperature after this initial replacement of one of the R' groups on the starting phosphite up to a limit of about 150° C. and most preferably up to about 120° C. As stated above, the point at which the temperature should be raised can be determined by monitoring the amount of by-product alkanol produced. Thus, when one mole of trimethyl phosphite is being transesterified, the reaction temperature can be raised after one mole of methanol has been evolved. The transesterification is completed when two moles of methanol have been evolved. The degree of polymerization of the polyphosphite can be controlled to an extent by varying the time of the reaction. Furthermore, the polymer length can be monitored by measuring the viscosity buildup during the reaction according to well known techniques.

The transesterification reaction can optionally be carried out in the presence of an inert solvent, however, such solvent is not required for the practice of the present invention. The term inert solvent is meant to designate any solvent which does not react with the starting materials or products of the present invention. Suitable solvents include the alkylated benzenes such as ethyl benzene, diethyl benzene, toluene, the xylenes, and substituted benzenes such as o-dichlorobenzene, chlorobenzene, anisole and the like.

The polyalkylene glycol alkyl or haloalkyl polyphosphite produced by the process described above and represented by Formula II, is then heated in the presence of an Arbuzov rearrangement catalyst whereby a rearrangement is effected and the polyalkylene glycol alkyl or haloalkyl polyphosphonate of Formula I above is formed. This rearrangement reaction may be carried out over a wide temperature range. Generally, temperatures from about 160° to about 230° C. are employed, with the preferred range being from about 165° to about 200° C. Although, any Arbuzov rearrangement catalyst may be employed, the alkyl halides and aralkyl halides are preferred. Illustrative of these are, for example, methyl iodide, ethyl iodide, methyl bromide, methyl chloride, butyl iodide, butyl chloride, aryl iodide, nonyl bromide, octyl iodide, benzyl bromide, benzyl iodide, chloromethylnapthalene, triphenylbromomethane, and the like. Methyl iodide is most preferred. Among other Arbuzov rearrangement catalysts are included elemental iodide and alkali metal halides, such as sodium iodide, potassium iodide, potassium fluoride, sodium bromide, lithium iodide, and the like. Any catalytically effective amount of the catalyst may be employed and generally is in the range of from about 0.05% to about 5% by weight. Preferably from about 0.1% to about 0.2% of catalyst is used.

Similar to the transesterification reaction described above, the rearrangement of the polyalkylene glycol alkyl or haloalky polyphosphite can optionally be carried out in the presence of an inert solvent, however, such solvent is not required for the practice of the present invention. Thus, the same solvent as employed during the transesterification reaction or a different solvent may be used during the rearrangement reaction. Suitable solvents include the alkylated benzenes such as ethyl benzene, diethyl benzene, toluene, the xylenes and substituted benzenes such as o-dichlorobenzene, chlorobenzene, anisole and the like. Furthermore, in performing the rearrangement reaction, the catalyst may be added all at once or in increments to the polyalkene glycol alkyl or haloalkyl polyphosphite intermediate. Moreover, if a solvent is being employed, a mixture of said solvent and catalyst may be added in increments. When a solvent is being employed, the rearrangement is generally completed in from about 2 to about 20 hours, whereas the reaction is completed in from about 5 minutes to about one hour in the absence of a solvent, depending upon the temperature being employed. The final product, i.e. the polyalkylene glycol alkyl polyphosphonate is essentially neutral and generally does not have an acid number in water in excess of 15 miligrams of KOH per gram of sample (in water). Accordingly, there is no need to neutralize the polyalkylene glycol alkyl or haloalkyl polyphosphonates prepared according to the present invention. However, if desirable, the polyalkylene glycol alkyl or haloalkyl polyphosphonate may be further neutralized by employing any of the conventional means to do so, such as treatment with ethylene oxide, propylene oxide, epichlorohydrin and the like.

The novel polyalkylene glycol alkyl or haloalkyl polyphosphonates of the present invention are particularly characterized by their ability to copolymerize with polyisocyanates employed in forming polyurethanes, by their relatively low OH numbers and low acidity, by their high phosphorus content, and by their high flame retardant and stabilized characteristics especially in the final foams. These compounds can completely replace the polyols normally employed in forming the urethane foams or they can be used in combination with the polyols, thereby yielding foams with greatly improved flame resistance. Since they react in the foam forming process, their residues are chemically bonded into the foam, thereby giving them high performance such as durability, even upon high temperature aging or after water or solvent extraction. As stated above, the acid numbers in water of the polyalkylene glycol alkyl or haloalkyl polyphosphonates of the present invention are generally in the range of from essentially neutral to about 15 milligrams of KOH per gram of sample, and most usually from essentially neutral to about 2 milligrams of KOH per gram of sample. This lack of or low acidity, in contrast to the higher acidity of prior art compounds, makes the compounds of the present invention essentially unreactive toward the polymerization catalysts employed in producing the polyurethane foams. As mentioned above, the present compounds also have relatively lower OH numbers as compared to the prior art flame retardants and, therefore, can be used in flexible urethane foams without materially affecting the physical properties of such foams. By the term relatively low OH numbers, it is meant to designate OH numbers below about 150 and preferably below 100. The compounds of the present invention are further characterized by the fact that they are substantially linear polymers when compared to those disclosed in the prior art.

The polyalkylene glycol alkyl or haloalkyl polyphosphonates of the present invention, when employed in sufficient quantity, will yield a self-extinguishing polyurethane foam. This characteristic is particularly important in the area of flexible foams due to the wide use of such foams in hospitals, homes and automobiles. Normally, the compounds of the present invention can be employed in amounts of from about 3 to about 30 percent, by weight, of the entire foam forming mixture to yield self-extinguishing foams. Preferably, they are employed in amounts from 3 to 10 percent, by weight, of the entire mixture. It is understood, however, that this amount will vary depending upon the particular foam being used, and that the required proportions can easily be determined with a minium amount of blending work.

While the compounds of the present invention are primarily intended for use in urethane foams, it is contemplated that they can also be used in a wide variety of polymeric systems. Illustrative of these systems are: polyester, polyolefins, cellulose ethers and esters, urethane coatings and elastomers, polymethyl methacrylates, polyvinyl chlorides, and many others. Furthermore, the compounds of the present invention can also be employed in combination with any of the known flame retardants for foams or polymeric system such as, for example, tris(dichloropropyl) phosphite, tris(chloroethyl) phosphite, tris(dibromopropyl) phosphite, and the like.

The polyurethane foams within which the flame retardants described above are incorporated are well known in the art. They are produced by the reaction of a di- or polyisocyanate and a di- or polyhydroxy (polyol) compound in the presence of a blowing agent and a catalyst. The foams can be made by any of the basic techniques used in foam formation; i.e. the prepolymer technique, the semi-prepolymer technique or the one-shot process. These techniques are well known and described in the polyurethane art.

As examples of organic di- and polyisocyanates which can be employed to make the polyurethane foams there can be employed toluene-2,4-diisocyanate; toluene-2,6-diisocyanate; 4-methoxy-1,3-phenylene diisocyanate; diphenyl methane-4,4'-diisocyanate; 4-chloro-1,3-phenylene-diisocyanate; 4-isopropyl-1,3-phenylene-diisocyanate; 4-ethoxy-1,3-phenylene-diisocyante; 2,4-diisocyanate-diphenylether; 3,3'-dimethyl-4,4'-diisocyanatodiphenyl methane; mesitylene diisocyanate; durylene diisocyanate; 4,4'-methylene-bis (phenylisocyanate); benzidine diisocyanate; o-nitrobenzidine diisocyanate; 4,4'-diisocyanatedibenzyl; 3,3'-bitolylene-4,4'-diisocyanate; 1,5-naphthalene diisocyanate; tetramethylene diisocyanate; hexamethylene diisocyanate; decamethylene diisocyanate; toluene-2,4,6'-triisocyanate; tritolylmethane triisocyanate; 2,4,4'-triisocyanatodiphenyl ether; the reaction product of toluene diisocyanate with trimethylolpropane; and the reaction product of toluene diisocyanate with 1,2,6-hexanetriol.

Alternatively, as the polyisocyanate there can be used prepolymers made by reacting one or more of the above polyisocyanates with a di- or polyhydroxy compound such as a polyester having terminal hydroxyl groups, a polyhydric alcohol, glycerides or hydroxy containing glycerides, etc. These prepolymers should have terminal isocyanate groups and, to insure their presence, it is frequently desirable to employ an excess of 5% or more of the polyisocyanate in forming the prepolymer. Typical examples of such prepolymers having isocyanate and groups are those formed from toluene diisocyanate and polyhydroxy compounds. In most cases, a mixture of 80% of the 2,4-isomer and 20% of the 2,6-isomer of toluene diisocyanate is employed in making these prepolymers. Thus, there can be used the prepolymers resulting from the reaction between toluene diisocyanate and caster oil, blown tung oil, blown linseed or blown soya oil, and of toluene diisocyanate and the polyester of ethylene glycol, propylene glycol and adipic acid.

Examples of suitable polyols are polyethylene glycol, polypropylene glycols, ethylene glycol, diethylene glycol, triethylene glycol, propylene glycol, dipropylene glycol, tripropylene glycol, 1,4-butanediol, thiodiglycol, glycerol, trimethylolethane, trimethylolpropane, ether triols from glycerine and propylene oxide, other containing triols from 1,2,6-hexanetriol and propylene oxide, sorbitol-propylene oxide adducts, pentaerythritol-propylene oxide adducts, trimethylol phenol, oxypropylated sucrose, triethanolamine, pentaerythritol, diethanolamine, castor oil, blown linseed oil, blown soya oil, N,N,N',N'-tetrakis(2-hydroxyethyl) ethylenediamine, N,N,N',N'-tetrakis(2-hydroxypropyl) ethylenediamine, N,N,N',N'',N''pentakis(2-hydroxypropyl) diethyl triamine, N,N,N',N'',N'''-pentakis(2-hydroxyethyl) diethylene triamine, mixed ethylene glycolpropylene glycol adipate resin, polyethylene adipate phthalate and polyneopentylene sebacate.

In preparing the foamed polyurethanes there can be used any of the conventional basic catalysts such, for example, as N-methyl morpholine, N-ethyl morpholine, 1,2,4-trimethylpiperazine, trimethyl amine, triethyl amine, tributyl amine and other trialkyl amines, the esterification product of adipic acid and diethylethanolamine, triethyl amine citrate, 3-morpholinopropionamide, 1,4-bis(2-hydroxypropyl)-2-methylpiperzine, 2-diethylaminoacetamide, 3-diethylaminopropionamide, diethylethanolamine, triethylenediamine, N,N,N',N'-tetrakis (2-hydroxypropyl) ethylenediamine, N,N'-dimethylpiperazine, N,N-dimethylhexahydroaniline, tribenzylamine and sodium phenolate. Also applicable are tin compounds, e.g. hydrocarbon tin alkyl carboxylates such as dibutyltin dilaurate, dibutyltin diacetate, dibutyltin dioctoate, tributyltin monolaurate, dimethyltin diacetate, dioctyltin diacetate, dilauryltin diacetate, dibutyltin maleate, hydrocarbon tin alkoxides, e.g. dibutyltin diethoxide, dibutyltin dimethoxide, diethyltin dibutoxide as well as other tin compounds, e.g. octylstannoic acid, trimethyltin hydroxide, trimethyltin chloride, triphenyltin hydroxide, trimethyltin chloride, triphenyltin hydride, triallyltin chloride, trioctyltin fluoride, dibutyltin dibromide, bis-(carboethoxymethyl) tin diiodide, tributyltin chloride, trioctyltin acetate, butyltin trichloride, octyltin tris(thiobutoxide), dimethyltin oxide, dibutyl tin oxide, dioctyltin oxide, diphenyltin oxide, stannous octanoate, and stannous oleate.

Any of the conventional surfactants can be used in amounts of 1% or less, e.g. 0.2% by weight of the composition. The preferred sufactants are silicones, e.g. polydimethyl siloxane having a viscosity of 3 to 100 centistokes, triethoxydimethyl polysiloxane, molecular weight 850 copolymerized with a dimethoxypolyethylene glycol having a molecular weight of 750.

The foaming reaction can be carried out by adding water to the polyol prior to or simultaneously with the addition of the polyisocyanate. Alternatively, foams can be prepared by the use of a foaming or blowing agent. These are usually a liquefied, halogen substituted alkane such, for example, as methylene chloride. Especially preferred are those halogen substituted alkanes having at least one fluorine atom in their molecules such as trichlorofluoromethane, dichlorodifluoromethane, dichloromonofluoromethane, chlorodifluoromethane, dichlorotetrafluoroethane. In using these blowing agents, they are uniformly distributed in either the polyol reactant or the polyisocyante reactant whereupon the reactants are mixed permitting the temperature of the mixture to rise during the ensuing reaction above the boiling point of the liquefied gas so as to produce a porous polyurethane. It should be noted that foaming may also be affected by combining the use of a blowing agent with the addition of water to the polyol.

Having generally described the invention, the following examples are given for purposes of illustration. It will be understood that the invention is not limited to these examples but is susceptible to different modifications that will be recognized by one of ordinary skill in the art.

EXAMPLE 1

To a 30 gallon reactor is charged 50.6 pounds of diethylene glycol, 65.6 pounds of trimethylphosphite, 123 pounds of O-dichlorobenzene and 48 grams of sodium methoxide (25% solution in methanol). The reaction mixture is heated (in a nitrogen atmosphere) to about 100° C. and maintained at their temperature for about 2¼ hours with removal of volatiles. A vacuum is slowly applied to the reactor (to 54 mm Hg) with the temperature cooling to 180° F., the volatiles are further stripped in this manner for 45 minutes.

To the resultant product is added 120 grams of methyl iodide and 14 pounds of O-dichlorobenzene. The resultant mixture is heated (in a nitrogen atmosphere) to reflux and held at about 165° C. for ½ hour. The reaction temperature is increased to about 180° C. and maintained there for an additional 7½ hours with removal of volatiles. The product obtained is a viscous clear colorless liquid with an acid number of 0.54 milligrams of KOH per gram of sample in water and neutral in $CH_3OH$. Analysis of the product confirmed the structure to be poly(diethylene glycol methylphosphonate), having an average n value of 6.5.

Analysis: % P = 17.9 OH Number = 62.

EXAMPLE 2

To a 0.5 liter 3-necked round bottom flask equipped with a mechanical stirrer, thermometer and distillation head is charged 106 grams (1 mole) of diethylene glycol, 136.4 grams (1.1 moles) of trimethylphosphite and 0.25 grams of sodium methoxide (25% in methanol). The reaction mixture is vigorously agitated while it is heated to from about 100° to 110° C. and it is maintained at about 110° C. until about 70 to 80% of the theoretical quantity of methanol is evolved, i.e. about 2 hours. The reaction mixture is further stripped of volatiles by gradually reducing the pressure inside the flask to about 120 mm Hg by aspirator.

To the resultant product is added 0.5 grams of methyl iodide in 100 milliliters of O-dichlorobenzene. The resultant mixture is heated (in air) to reflux at 180° C. and maintained at this temperature for 8 hours. The reaction mixture is cooled to about 100° to 110° C. It is essentially neutral, however, ethylene oxide is introduced to remove most of the residual acidity. The volatiles are removed from the reaction mixture by distillation at 110° C. and 8-15 mm Hg. The product is a viscous clear colorless liquid and is obtained in about 80-90% yield.

Analysis of the product confirmed the product to be poly(diethylene glycol methylphosphonate) having an average n value of 14.

Analysis: % P = 18.0 (Theory 19.6); Acid No. = 0.3 mg KOH/g sample in water; Acid No. = nil in $CH_3OH$; OH No. = 60; Infrared analysis revealed OH, P=O and P—$CH_3$; bonds at 3450 cm$^{-1}$, 1230 cm$^{-1}$, and 1310 cm$^{-1}$, respectively.

EXAMPLE 3

A flask fitted with a mechanical stirrer, thermometer, and distillation head is charged with 212 grams (2.0 moles) of diethylene glycol, 332 grams (2.0 moles) of triethylphosphite, and 0.16 grams Na in 5 milliliters of methanol. The reaction mixture is vigorously agitated and heated to from about 120° C. to 135° C. over a period of about 3 hours. The reaction is further stripped of volatiles under aspirator vacuum at a temperature of about 90° to 100° C.

The remaining product is dissolved in 150 grams of O-dichlorobenzene to which 1.3 grams of methyl iodide is added. The mixture is heated (in air) to reflux and maintained at a temperature of about 170°-180° C. for about 5 hours. The solvents are removed under aspirator pressure at a temperature of about 80°-110° C. for about 1½ hours, with removal of volatiles. The product obtained is a viscous clear colorless liquid having an acid number in water of 8.12 mg of KOH per gram of sample. Analysis of the product confirmed the product to be poly(diethylene glycol ethylphosphonate):

Analysis: % P + 17.1 OH No. + 94.

EXAMPLE 4

To a liter flask equipped with a mechanical stirrer, thermometer and distillation head is charged 402 grams (3.0 mole) of dipropylene glycol, 409.2 grams (3.3 mole) of trimethyl phosphite and 0.8 grams of sodium methoxide (25% methanol). The reaction mixture is stirred and heated to about 110° C. while 166 grams of volatiles are collected. The reaction mixture is then further stripped of volatiles under aspirator pressure.

To the remaining product is added 400 grams of O-dichlorobenzene. This reaction mixture is cooled to room temperature and 1.0 grams of methyl iodide is added. The mixture is heated to 105° C. for 2½ hours. The temperature is raised to 180° C. and the reaction is continued for another 4 hours. The remaining volatiles are stripped under aspirator pressure. The resultant product has an acid number in water of 1.68 mg of KOH per gram of sample. Analysis of the product confirms the product to be poly(dipropylene glycol methylphopshonate).

Analysis. OH No. = 46 % P = 14.9.

EXAMPLE 5

This example illustrates the preparation of the intermediate poly(diethylene glycol methylphosphite).

To a 5 liter flask fitted with a mechanical stirrer, thermometer, and distillation head is added 1,802.0 grams (17.0 moles) of diethylene glycol and 2,318.8 grams (18.7 moles) of trimethyl phosphite. The reaction mixture is stirred and heated to a temperature of 110° C. in the absence of a transesterification catalyst while collecting volatiles for about 4½ hours. The reaction mixture is further stripped under aspirator pressure for about ½ hour. The product is collected in 95% yield.

EXAMPLE 6

The product made according to the procedure of Example 1 is incorporated into a polyurethane foam formulation as set forth in Table I, below.

TABLE I

| | |
|---|---|
| Polyol (Voranol CP 3000, made by Dow Chemical Co. a 3000 molecular weight propoxylated glycerol) | 700 gms |
| Poly(diethylene glycol methylphosphonate) prepared according to Example 1 | 49 gms |
| Water | 28 gms |
| Silicone surfactant L-548 made by Union Carbide | 7 gms |
| N-ethyl morpholine | 0.66 gms |
| 67% dimethylaminoethyl ether in dipropylene glycol | 0.46 gms |
| 33% 1,4-diazobicyclo [2.2.2] octane in dipropylene glycol | 0.98 gms |
| Stannous octoate, 50% in dioctyl phthalate | 2.8 gms |
| Toluene diisocyanate (80/20 isomers) | 370 gms |
| FOAM PROPERTIES | |
| Color | White |
| Odor | None |
| Density - (lb./ft³) | 1.47 |
| Air flow - (ft.³/min.) | 2.1 |
| Indent Load Deflection - (ILD, 25% lb.) | 25 |
| FOAM FLAMMABILITY | |
| Motor Vehicle Safety Standard (MVSS 302) Initial | SE/NBR (self-extinguishing, no burning rate) |

EXAMPLE 7

The product made according to the procedure of Example 4 is incorporated into a polyurethane foam formulation as set forth in Table II, below.

TABLE II

| | |
|---|---|
| Polyol (Voranol CP 3000) | 750 gms |
| Poly(dipropylene glycol methylphosphonate) according to Example 4 | 75 gms |
| Water | 30 gms |
| Silicone surfactant L-548 | 7.5 gms |
| N-ethyl morpholine | 1.2 gms |
| 67% dimethylaminoethyl ether in dipropylene glycol | 0.8 gms |
| 33% 1,4-diazobicyclo [2.2.2] octane in dipropylene glycol | 1.8 gms |
| Stannous octoate, 50% in dioctyl phthalate | 3.0 gms |
| Toluene diisocyanate (80/20 isomers) | 418 gms |
| FOAM PROPERTIES | |
| Color (initial) | Yellow |
| Odor | Some |
| Density - (lb./ft.³) | 1.41 |
| ILD, 25% lb. | 29 |
| 65% lb. | 60 |
| FOAM FLAMMABILITY | |
| MVSS 302 Initial | SE |
| Dry heat 72 hrs/ 93° C. | SE |

What is claimed is:

1. The process of preparing a polyalkylene glycol alkyl or haloalkyl polyphosphonate composition characterized by an acid number in water of below about 15 mg. of KOH per gram of sample and having the formula:

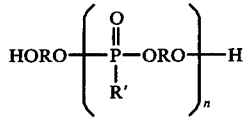

wherein R is the residue of a polyalkyl glycol having the formula:

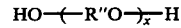

wherein R" is an alkylene radical of 2 to 20 carbon atoms and x is number from 2 to about 20, R' is alkyl or haloalkyl and n is a number in the range from about 2 to about 50 comprising heating a polyalkylene glycol alkyl or haloalkyl polyphosphite of the formula:

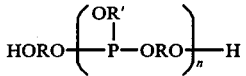

wherein R, R' and n are as defined above in the presence of a catalytically effective amount of an Arbusov rearrangement catalyst at a temperature in the range from about 160° to 230° C.

2. The process of claim 1 wherein said polyalkylene glycol aklyl or haloalkyl polyphosphite is selected from the group consisting of diethylene glycol alkyl or haloalkyl polyphosphite, dipropylene glycol alkyl or haloalkyl polyphosphite, triethylene glycol alkyl or haloalkyl polyphosphite, tripropylene glycol alkyl or haloalkyl polyphosphite and tributylene glycol alkyl or haloalkyl polyphosphite.

3. The process of claim 1 wherein said polyalkylene glycol alkyl polyphosphite is diethylene glycol methyl polyphosphite and said Arbuzov rearrangement catalyst is methyl iodide.

4. The process of claim 3 wherein said diethylene glycol methyl polyphosphite is prepared by transesterifying trimethyl phosphite with diethylene glycol in a mole ratio of about 1.1 to 1, respectively.

5. A process for the preparation of polyalkylene glycol alkyl or haloalkyl polyphosphite having the formula:

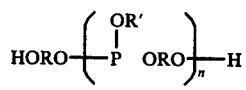

wherein R is the residue of a polyalkylene glycol having the formula:

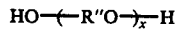

wherein R″ is an alkylene radical of 2 to 20 carbon atoms and $x$ is a number from 2 to about 20, R′ is alkyl or haloalkyl and $n$ is a number in the range from about 2 to about 50 which consists of transesterifying a tertiary phosphite having the formula:

wherein R′ is as defined above with a polyalkylene glycol having the formula:

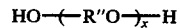

wherein R″ and $x$ are as defined above in a mole ratio from about 0.8 to 1 to about 1.5 to 1 at a temperature from about 20° to about 150° C.

6. The process of claim 5 wherein said polyphoshite is diethylene glycol methyl polyphosphite, said phosphite is trimethyl phosphite and said glycol is diethylene glycol.

7. The process of claim 5 wherein said trimethyl phosphite and diethylene glycol are in the mole ratio of about 1.1 to 1, respectively.

* * * * *